United States Patent
Walter et al.

(10) Patent No.: US 6,248,564 B1
(45) Date of Patent: *Jun. 19, 2001

(54) MUTANT MHC CLASS I MOLECULES

(75) Inventors: Jürgen B. Walter, Erlangen (DE); David N. Garboczi, Gaithersburg, MD (US)

(73) Assignee: Harvard University, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/920,413

(22) Filed: Aug. 29, 1997

(51) Int. Cl.⁷ .......................... C12P 21/04; G01N 33/53; C07K 1/00; A61K 39/40
(52) U.S. Cl. .................. 435/69.7; 424/93.7; 424/178.1; 424/193.1; 435/69.6; 530/336; 530/380; 530/387.3; 530/395; 530/402; 530/404
(58) Field of Search ..................................... 435/7.24, 7.5, 435/69.6, 69.7; 530/336, 380, 402, 404, 387.3, 391.1, 395; 424/178.1, 93.7, 193.1

(56) References Cited

U.S. PATENT DOCUMENTS

| | | |
|---|---|---|
| 4,400,376 | 8/1983 | Sanderson . |
| 4,478,823 | 10/1984 | Sanderson . |
| 4,698,420 | 10/1987 | Urnovitz . |
| 5,130,297 | 7/1992 | Sharma et al. . |
| 5,153,265 | 10/1992 | Shadle et al. . |
| 5,635,363 * | 6/1997 | Altman et al. . |

FOREIGN PATENT DOCUMENTS

| | | |
|---|---|---|
| 0352761A2 | 1/1999 | (EP) . |
| WO 96/26962 | 9/1996 | (WO) . |

OTHER PUBLICATIONS

Fukazawa et al. J. of Immunology 153: 3543, 1994.*
Parleen et al. Biochemistry 22: 1145, 1983.*
Vessey et al. Eun. S. Immunol. 22: 879, 1997 (Apr.).*
Shields et al Molecular Immunology 35:919–928 1998.*
Saraswat et al J. of Biological Chemistry, 266(29):1777–19785 1991.*
Weir et al., "Chapters 3 Haptens and Carriers", Handbook of Immunology 4th edition: Immunochemistry, published 1986, Blackwell Scientific Publications, Oxford, UK pp. 3.1–3.13.
Altman et al., "Phenotypic Analysis of Antigen–Specific T Lymphocytes", Science 274:94–96, 1996.
Eisen et al., "Antigen–Specific T–Cell Receptors and Their Reactions with Complexes . . .", Advances in Protein Chemistry 49:1–56, 1996.
Garboczi et al., "Assembly, Specific Binding, and Crystallization of a Human TCR–$\alpha\beta$ with an . . .", J. Immunol. 157:5403–5410, 1996.
Garboczi et al., "HLA–A2–peptide complexes: Refolding and crystallization of molecules expressed in . . .", Proc. Natl. Acad. Sci. USA 89:3429–3433, 1992.
Parker et al., "Localization of the Sites of Iodination of Human . . .", Biochemistry 22:1145–1153, 1983.
Rupert–Vessey et al., "Engagement of a T cell Receptor by major histocompatibility . . ." Eur. J. Immunol. 27:879–885, 1997.
Sykulev et al., "High–affinity reactions between antigen–specific T–cell receptors and peptides . . .", Proc. Natl. Acad. Sci. USA 91:11487–11491, 1994.
Tysoe–Calnon et al., "Molecular comparison of the $\beta_2$–microglobulin . . ." Biochem. J. 277:359–369, 1991.
Walter et al., "Stimulation of human cytotoxic T cells with HIV–1–derived peptides . . ." International Immunology 9:451–459, 1997.
Zhang et al., "Crystal structure of the major histocompatibility complex class I . . .", Proc. Natl. Acad. Sci. USA 89:8403–8407, 1992.

* cited by examiner

*Primary Examiner*—David Saunders
*Assistant Examiner*—Amy DeCloux
(74) *Attorney, Agent, or Firm*—Fish & Richardson P.C.

(57) ABSTRACT

Methods of generating a conjugate of MHC class I molecule and a compound via a cysteine residue engineered into the $\beta$2-M subunit. Also featured are uses of the conjugates.

31 Claims, 4 Drawing Sheets

MUTANT MHC CLASS I MOLECULES

STATEMENT AS TO FEDERALLY SPONSORED RESEARCH

The invention was funded in part by National Institutes of Health grant Nos. NOIAI 45218, ROIAI 28568, AI 34247, and CA 60686, and the Department of the Army grant No. DAMD17-94-J-4060. The government may have certain rights in the invention.

BACKGROUND OF THE INVENTION

The major histocompatibility complex ("MHC") plays a central role in the immune system. Antigen-specific T cells recognize antigenic peptides in association with MHC class I or II molecules on the cell surface. Class I molecules consist of two noncovalently associated subunits: a highly polymorphic α heavy chain and a conserved β2-microglobulin ("β2-M") light chain. Two of the three extracellular domains of the heavy chain, i.e., domains β1 and α2, are folded into a "groove" structure which anchors an antigenic peptide for presentation to T cells.

Human class I molecules (or "complexes") have been refolded from *E. coli*-produced heavy chains and β2-M subunits in the presence of synthetic peptides (Garboczi et al., *Proc. Natl. Acad. Sci. USA*, 89:3429–3433, 1992). The three-dimensional structures of such recombinant complexes as determined by X-ray crystallography are virtually identical to the structure of the class I molecule as isolated from human cells (Madden et al., *Cell*, 75:693–708, 1993; Bjorkman et al., *Nature*, 329:506–512, 1987). Further, subtype A0201* of HLA-A2 produced in *E. coli* and assembled with synthetic HIV-1 nonapeptides has been shown to elicit cytolytic CD8⁺T cell responses (Walter et al., *Int. Immunology*, 9:451–459, 1997).

The classical class I gene family includes the highly polymorphic human class I molecules HLA-A, -B, and -C, and murine class I (i.e., H-2) molecules D, K, and L. A series of structural relatives (non-classical class I molecules) has been found in humans (e.g., HLA-E, -F, -G, -H, -I, and -J; and CD1) and mice (Q, T, M, and CD1) (Shawar et al.,*Annu. Rev. Immunol.*, 12:839–880, 1994). These molecules have the typical structure of an antigen-presenting molecule, where a polymorphic heavy chain is noncovalently associated with the conserved β2-M subunit. The T cell repertoire reacting with these non-classical ligands has been characterized to only a limited extent.

SUMMARY OF THE INVENTION

The invention features a method of preparing a conjugate of an MHC class I molecule and a compound. In this method, one first obtains an MHC class I molecule, where a cysteine residue (i.e. a non-natural or new cysteine residue) has been engineered into its β2-microglobulin subunit. The compound (e.g., a protein, a carbohydrate, a lipid molecule, or any other organic compound) is then conjugated to the mutant class I molecule specifically via a linkage formed between the sulfhydryl group of the new cysteine residue in the β2-microglobulin subunit and a functional group of the compound. Alternatively, the compound can be first conjugated to the new β2-M subunit, and then the subunit is mixed with an α heavy chain (from the same or different species as the β2-M subunit) in the presence of an appropriate peptide to form a compound-class I conjugate. The cysteine residue is preferably introduced into a region of β2-M that faces away from the interface between β2-M and the α heavy chain. Exemplary regions are those corresponding to residues 15–23, 35–53, or 66–97 of SEQ ID NO: 1. SEQ ID NO: 1 shows the amino acid sequence of a human β2-M. Minor sequence variations can exist among β2-M molecules from different or the same species; and residues from two different β2-M sequences are said to be corresponding to each other when they are equivalent in function or relative position to the conserved residues in the two β2-M sequences, or both. The new residue, alone or together with one or more (e.g., two to five) amino acid residues, can be inserted into the β2-M region without any deletion of the region, or replace one or more (e.g., two to five) residues of the region. For instance, the new cysteine residue can replace a residue that corresponds to serine 52, tyrosine 67, or lysine 91 of SEQ ID NO: 1.

The compound can be, for example, a ligand for a multivalent binding molecule, an antibody (e.g., one that is specific for a tumor antigen), a molecule on the surface of a cell (e.g., an antigen-presenting cell or any other hematopoietic cell), or a ligand for a surface receptor of a cell.

The new compound-class I conjugates have several uses. For instance, when a multivalent binding molecule is supplied, conjugates of the ligands for the binding molecule with the new, monomeric class I molecules (e.g., ones that consist of an α heavy chain, the new β2-M, and a peptide associated with the heavy chain) can be multimerized. Multimeric class I molecules can be used to, e.g., label, isolate and quantitate specific T cells. Exemplary multivalent binding molecules are avidin (or a derivative thereof, e.g., streptavidin), whose ligands are biotin and biotin derivatives.

A conjugate of the present invention can also be used to stimulate the immunity of an individual (e.g., a human or a mouse). To accomplish this, a conjugate of a new class I molecule and a cell (e.g., an antigen-presenting cell) is introduced into an individual, and the conjugate can stimulate the immune cells, particularly T cells specific for the peptide in the conjugate. In this method, the cell and the class I molecule in the conjugate are preferably syngeneic with this individual.

Another conjugate of the present invention can be used to eradicate a tumor (or any other undesired cell) in an individual. In this method, a conjugate of a new class I molecule and an antibody specific for an antigen (or a ligand for a receptor) expressed exclusively or primarily on the cell is introduced into the individual. The α heavy chain in the conjugate can be allogeneic or xenogeneic) to the patient. If the heavy chain is syngeneic to the patient, the class I molecule would be associated with an antigenic peptide that can elicit a strong T cell response.

Use of the new recombinant β2-M, monomeric and multimeric class I molecules containing the new β2-M, and the new compound-class I conjugates are also within the scope of the invention.

The new β2-M eliminates the need for genetically engineering MHC heavy chains to create a chemically reactive site in each of the differing MHC class I molecules. This is a significant advantage in view of the enormous polymorphism of MHC heavy chains.

Other features and advantages of the invention will be apparent from the following detailed description, and from the claims.

DETAILED DESCRIPTION

Figure 1A:
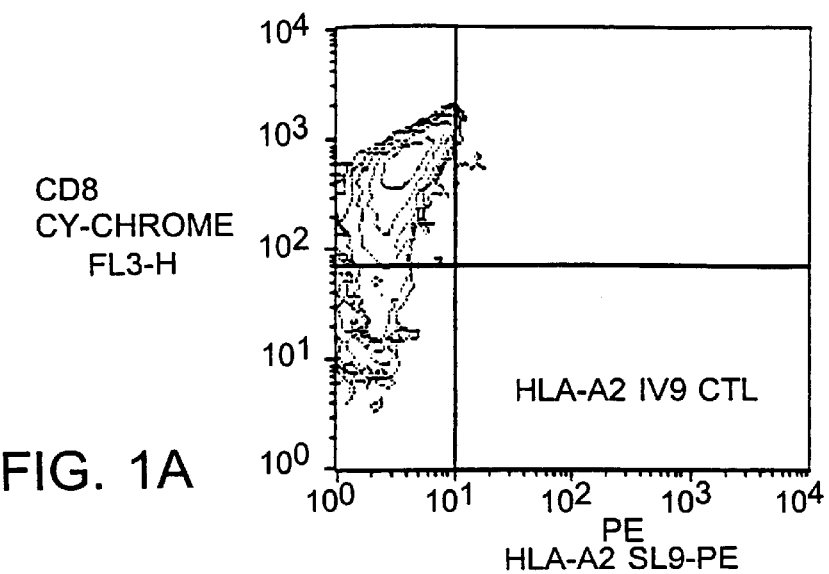
FIGS. 1A–1C are a set of graphs showing the results of flow cytometry analysis of the binding of the phycoerythrin-labeled HLA-A2-SL9 tetramer to human cytotoxic T lymphocyte cells of clones 68A62 (specific for HLA-A2-IV9), 18O30 (specific for HLA-A2-SL9), and 63D35 (specific for HLA-B11-AK9), respectively. The cells were also stained with an anti-CD8 monoclonal antibody that was labeled with Cy Chrome, i.e., a fluorescent complex of phycoerythrin and Texas Red.

Methods are provided for preparing a conjugate of a MHC class I molecule and a compound. The MHC class I molecule contains a recombinant β2-M subunit in which a cysteine residue has been introduced. This residue is preferably introduced into a region of β2-M that does not interact with the α heavy chain. Standard mutagenesis techniques can be employed to generate DNA encoding such mutant β2-M molecules. General guidance can be found in Sambrook et al., *Molecular Cloning, A Laboratory Manual*, Cold Spring Harbor Laboratory Press, Cold Spring Harbor, N.Y., 1989; and Ausubel et al., *Current Protocols in Molecular Biology*, Greene Publishing and Wiley-Interscience, New York, N.Y., 1993. The cysteine residue introduced into the β2-M subunit provides a convenient site for highly selective chemical modification. In addition, coupling between sulfhydryls and certain functional groups is reversible, allowing a compound to be released from the class I molecule to which it has been conjugated.

The compound can be linked to the new cysteine residue in the class I molecule via a functional group of its own. Sulfhydryl-reactive functional groups include, but are not limited to, maleimides, pyridyl disulfide, α-haloacyl derivatives (e.g., iodoacetamides), alkyl halides, and aryl halides. Maleimides, alkyl and aryl halides, and α-haloacyls react with sulfhydryls to form thiol ether bonds. Pyridyl disulfides, on the other hand, react with sulfhydryls to produce mixed disulfides. The pyridyl disulfide product is cleavable. A sulfhydryl-reactive crosslinker can also be used, especially when the compound does not contain any sulfhydryl-reactive groups itself. Such a crosslinker possesses two or more different reactive groups that allow its sequential conjugations with two or more other molecules. For instance, crosslinkers that are amine-reactive at one part and sulfhydryl-reactive at another part (e.g., some DOUBLE-AGENT™ crosslinkers available from PIERCE, Rockford, Ill.) can be used to link an amine-containing compound with the mutant class I molecule. By way of example, N-Succinimidyl 3-(2-pyridyldithio)-propionate ("SPDP") is a reversible NHS-ester (i.e., N-hydroxysuccinamide-ester), pyridyl disulfide crosslinker; the amine-reactive NHS-ester in SPDP can be reacted first with a compound of interest, and then with the free —SH group of the new class I molecule. Useful water-soluble SPDP analogs include sulfosuccinimidyl 6-(3-[2-pyridyldithio]propionamido) hexanoate (i.e., sulfonating long chain SPDP analog or Sulfo-LC-SPDP), LC-SPDP, 4-Succinimidyloxycarbonyl-α-methyl-α-(2-pyridyldithio)-toluene ("SMPT"), and sulfosuccinimidyl-6-(α-methyl-α-[2-pyridyldithio]-toluamido) hexamoate ("Sulfo-LC-SMPT"). Additional sulfhydryl- and amine-reactive heterofunctional crosslinkers include succinimidyl-4-(N-maleimidomethyl)-cyclohexane-1-carboxylate ("SMCC"), N-γ-maleimidobutyryloxysulfosuccinimide ester, m-maleimidobenzoyl-N-hydroxysulfosuccinimide ester, sulfosuccinimidyl [4-iodoacetyl] aminobenzoate, and sulfo-succinimidyl 4-[p-maleimidophenyl] butyrate (Pierce, Ill.). Homobifunctional sulfhydryl-reactive crosslinkers such as Bis-maleimidohexane ("BMH"), 1,4-Di-(3'-[2'-pyridyldithio] propionamido-butane ("DPDPB"), and 1,5-difluoro-2,4-dinitrobenzene ("DFDNB") can also be used if the compound to be conjugated contains a sulfhydryl.

The α and β2-M subunits of the MHC class I protein can be from the same or different species (e.g., humans, rats, mice, hamsters, frogs, chickens, etc.). The transmembrane and optionally intracellular domains of the α subunit can be removed to promote proper in vitro folding. Methods for obtaining class I heavy chains and β2-M subunits and for forming monomeric class I-peptide complexes are well known in the art (see, e.g., Zhang et al., *Proc. Natl. Acad. Sci. USA*, 89:8403–8407, 1992; and Garboczi et al., *Proc. Natl. Acad. Sci. USA*, 89:3429–3433, 1992). The α and β2-M subunits obtained with a recombinant expression system (e.g., an *E. coli* or baculoviral system) can be refolded separately or together, and then associated in the presence of appropriate peptides (e.g., peptides of about 8–12 amino acid residues in length). Alternatively, the mutant β2-M subunit can be associated with the α subunit of a pre-formed class I molecule via exchange with the β2-M subunit in the pre-formed molecules; in such case, no peptide supply is needed in the association reaction if the pre-formed class I molecule is already occupied by a peptide.

In general, the conjugation between the class I protein and the compound is performed after the β2-M subunit has folded into a native or native-like conformation. In this conformation, the naturally occurring cysteine residues (4 in the heavy chain and 2 in β2-M) are engaged in stable disulfide bonds and hence not accessible for chemical modification. Therefore, conjugation occurs specifically via the unpaired, surface-exposed cysteine.

Described below are the generation and use of several conjugates of the invention. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, exemplary methods and materials are described below. These exemplary methods and materials are illustrative only and not intended to be limiting. All publications, patent applications, patents, and other references mentioned herein are incorporated by reference in their entirety. In case of conflict, the present specification, including definitions, will control.

I. Cell-Class I Conjugates

The new class I molecule can be conjugated to a compound (e.g., a protein, carbohydrate, or lipid molecule) on a cell surface via the new cysteine in the β2-M subunit. To accomplish this, the surface of the cell can be reduced in mild conditions with a reducing reagent (e.g., dithiothreitol ("DDT"), 2-mercaptoethanol, or 2-mercaptoethylamine.HCl), resulting in reactive sites (e.g., sulfhydryl groups) on the cell surface. Such reactive sites will then be reacted directly, or linked through a bifunctional crosslinker, with the free sulfhydryl group in the class I molecule. By way of example, the sulfonyl groups attached to the succinimidyl rings in Sulfo-NHS esters (e.g., Sulfo-LC-SPDP or Sulfo-SMCC) make these crosslinkers membrane-impermeable and thus non-reactive with inner membrane proteins; thus, these crosslinkers are useful in crosslinking the new class I complexes to the cell surface. To determine optimal conjugation conditions, class I negative cells such as human HMy2.C1R cells (American Type Culture Collection CRL-1993) can be used. The density of the class I peptide complexes anchored on the cell surface can be determined by fluorescence-activating cell sorting ("FACS") analysis, using monoclonal antibodies ("MAb"s) against the class I molecule.

Peptide-class I complexes conjugated to syngeneic cells can be used to stimulate the immunity in an individual. To do this, cells derived from this individual or an another with matching MHC haplotypes are conjugated in vitro to the new class I molecules that have been loaded with antigenic peptides of interest. Useful cells include, but are not limited to, peripheral blood lymphocytes taken from a Ficoll density gradient, purified antigen presenting cells such as macrophages/monocytes, dendritic cells, and B cells, or red blood cells. Antigenic peptides of interest are, for example, melanoma-associated immunodominant epitopes derived from melanoma-associated antigens such as MART-1/Melan A, gp 100/Pmel 17, tyrosinase, Mage 3, p15, TRP-1, and β-catenin (Tsomides et al., *International Immunol.*, 9:327–338). The cell conjugates are then introduced into the individual. If the conjugates are used for vaccination, it may be preferred to use antigen-presenting cells as the conjugates' cellular components, since these cells can provide the requisite costimulatory signals for inducing an effective T cell response.

The above immunization strategy allows the control of epitope density and circumvents a variety of problems associated with classical vaccination strategies. For instance, unlike traditional peptide vaccines, the peptides embedded in the present pre-formed, class I peptide complexes are protected from rapid enzymatic degradation or intracellular processing. Traditional peptide vaccines are generally not directly presented by class I molecules on the cell surface; instead, they are typically internalized and processed inside the cell for association with MHC class I molecules. Peptide presentation is thus dependent on a series of intracellular events including the rate of protein degradation, peptide transport, and competition with endogenous peptides.

EXAMPLE 1

Direct Conjugation of Class I Complexes with Cells $10^6$ cells in PBS are reduced with 50 μM DDT for 30 minutes. Consequently, reactive —SH groups on the cell surface are generated. After two washes with PBS, the reduced cells are incubated with the new class I complexes, resulting in formation of disulfide bonds between the —SH groups in the β2-M subunits and the —SH groups on the surface of the reduced cells.

EXAMPLE 2

Indirect Conjugation of Class I Molecules with Cells $10^6$ cells are suspended in 500 μl PBS buffer (pH 7.2), and 1 mg of Sulfo-SMCC is added to the cell solution. The incubation proceeds for an hour at room temperature or 30 minutes at 37° C., resulting in a covalent bond between the NHS-ester group in Sulfo-SMCC and a primary amine on the cell surface.

The cells are then washed three times with PBS, and incubated with 0.5 mg of the new recombinant class I protein at 4° C. for 1 hour. This step leads to formation of a covalent bond between the free —SH group in the new class I protein and the maleimide group in Sulfo-SMCC.

II. Antibody-Class I Conjugates

The new MHC class I molecule can be specifically targeted to a cell by conjugating to an antibody against an antigen expressed on the surface of the cell. For instance, non-self (e.g., allogeneic) class I molecules conjugated to antibodies specific for a tumor antigen (or any antigen exclusively or primarily expressed by any other undesired tissue) can be attached to tumor tissue (or the undesired tissue) in an individual. The tissue, which now bears foreign MHC molecules, becomes a target of allograft rejection, one of the strongest immune responses known, and can thereby be destroyed.

To elicit a strong immune response against undesired tissue in an individual, an antibody specific for the tissue can also be conjugated to a syngeneic MHC class I molecule that is associated with a potent T cell epitope (e.g., HLA-A2 with the influenza matrix protein 59-68 (ILGFVFTLTV, SEQ ID NO: 2), or the influenza B NP 85-94 (KLGEFYNQMM; SEQ ID NO: 3)). Such a conjugate can elicit a strong zcytotoxic T cell response that eradicates the undesired tissue.

A variety of monoclonal antibodies can be used to target tumor tissue. Exemplary tumor-associated antigens include, but are not limited to, the Lewisy-related carbohydrate (found on epithelial carcinomas), the IL-2 receptor p55 subunit (expressed on leukemia and lymphoma cells), the erbB2/p185 carcinoma-related proto-oncogene (overexpressed in breast cancer), gangliosides (e.g., GM2, GD2, and GD3), epithelial tumor mucin (i.e., MUC-1), carcinoembryonic antigen, ovarian carcinoma antigen MOv-18, squamous carcinoma antigen 17-1A, and malignant melanoma antigen MAGE. To extend the serum half life of the MHC-antibody conjugate, the antibody may be humanized if the tumor to be treated is in a human.

The antibody and the MHC components in the present conjugate are conjugated via a covalent bond between the new cysteine residue in the mutant β2-M and a functional group in the antibody. Intermediary crosslinkers can be used to form the covalent bond. For example, mild oxidation of the sugar moieties in an antibody, using, e.g., sodium metaperiodate, will convert vicinal hydroxyls to aldehydes or ketones. The reaction will be restricted to sialic acid residues when 1 mM sodium metaperiodate is used at 0° C. Subsequent reaction of the aldehyde or ketone group with a sulfhydryl-reactive, hydrazide-containing crosslinker (e.g., 3-(2-Pyridyldithiol)propionyl hydrazide ("PDPH"), 4-(N-maleimidomethyl)cyclohexane-1-carboxylhydrazide hydrochloride, or 4-(4-N-maleimidophenyl)butyric acid hydrazide hydrochloride) results in the formation of a hydrazone bond. The antibody can then be bonded to the new MHC class I molecule via a disulfide bond formed between the new cysteine residue in the β2-M and the sulfhydryl-reactive group in the crosslinker.

Alternatively, mild reduction of an immunoglobulin can generate free sulfhydryl groups from the disulfide bonds in the hinge region. The sulfhydryl groups can then be reacted with the free sulfhydryl group of the class I complex, either directly or via a homobifunctional crosslinker.

Antibody fragments (e.g., Fab, or F(ab)$'_2$ both of which lack the glycosylated Fc-portion) can also be conjugated to the class I complex. F(ab)$'_2$ fragments can be generated from antibody molecules by pepsin cleavage; these fragments can be linked through heterofunctional crosslinkers such as those that are amine- and sulfhydryl-reactive. Reduction of F(ab)$_2$ fragments generates Fab' fragments, which contain free sulfhydryl groups. These free sulfhydryl groups can be utilized in conjugation with the new class I proteins.

EXAMPLE

Generation of an Antibody-Class I Conjugate

The following is an exemplary protocol for conjugating an antibody to the new MHC class I molecule.

An immunoglobulin G ("IgG") stock solution is first prepared. It contains 2mg/ml IgG (i.e., 13 μM) in 0.1 M sodium acetate buffer (pH 5.5). The solution is stored at 0° C. To oxidize the antibody, 1 ml of the IgG stock solution is mixed with 0.1 ml of cold sodium metaperiodate solution (stock: 1 mM sodium periodate in 0.1 M sodium acetate buffer, pH 5.5) for 20 min at 0° C. in the dark. To stop the oxidation reaction, glycerol is added to reach a final concentration of 15 mM, and the incubation proceeds for 5 additional minutes at 0° C.

The IgG sample is then dialyzed over night against 0.1 M sodium acetate buffer (pH 5.5) and concentrated in a CENTRICON 30. The crosslinker PDPH is then added to the sample to a final concentration of 5 mM, and the sample is incubated for approximately 2 hours at room temperature.

The IgG protein attached to PDPH is purified by HPLC (i.e., high performance liquid chromatography) gel filtration. The HPLC running buffer is 0.1 M Tris-Cl (pH 8). The IgG peak fraction is concentrated with CENTRICON 30 to a final volume of 100 μl.

To prepare for the class I molecule in the MHC-antibody conjugate, 2 mg of HPLC-purified class I molecule is mildly reduced with a solution containing 0.1 mM DTT and 0.1 M Tris-Cl (pH 8) for 1 hour at room temperature. This will maintain the cysteine in a reduced state. The class I molecule preparation is then purified by HPLC, which removes DTT, and concentrated with CENTRICON 30.

2 mg of the resulting class I molecule is dissolved in 0.5 ml Tris-Cl (pH 8), and added to 0.5 ml of PDPH-modified IgG for overnight incubation at 4° C. The sample is then concentrated with CENTRICON 100 and the MHC-antibody conjugate so obtained, which is approximately 200 kD in size, is purified by HPLC gel filtration or fast protein liquid chromatography. The conjugate is concentrated with CENTRICON 100. Excess peptide (e.g., 5–15 fold molar excess) is added to the concentrated conjugate preparation to stabilize the class I molecule in the conjugate.

III. Multimeric MHC Class I Complexes

The new MHC class I molecule can also be used to form a multimeric MHC class I complex. To do so, one can first obtain a conjugate of a monomeric class I molecule and a ligand for a multivalent binding molecule. The conjugate is formed specifically via a linkage between the sulfhydryl group of the new cysteine in the β2-M subunit and a functional group of the ligand. Useful ligands include, but are not limited to, iodoacetyl-LC-biotin, N-(6-[Biotinamido] hexyl)-3'-(2'pyridyldithio)-propionamide ("biotin-HPDP"), and 1-Biotinamido-4-(4'-[maleimidomethyl] cyclohexane-carboxamido)butane ("Biotin-BMCC"). All these biotin derivatives bind to avidin (or a derivative thereof such as streptavidin), a tetravalent molecule. Quantitative blocking of the biotin-binding sites on avidin will render the avidin molecule mono-, bi-, or tri-valent. To generate the conjugate, the α and β2-M subunits may be allowed to associate in the presence of a peptide of interest to form a stable heteroduplex complex, and then be linked to the ligand; alternatively, the β2-M subunit may be-first linked to the ligand, and then allowed to associate with the α chain in the presence of the peptide. Multimers of these conjugates can be formed by supplying to these conjugates the multivalent binding molecule to which the ligand binds.

The multimeric MHC class I complexes can be used for labeling, quantitation, isolation, and stimulation of T cells. By way of example, the class I multimers can be immobilized on solid-phase matrices, generating an affinity support for the enrichment and isolation of T cells harboring the corresponding antigen receptors. The matrices may be, for instance, agarose gel, beaded polymers, polystyrene plates, glass slides, nitrocellulose membrane, or columns. Immobilization can be effected by non-covalent coupling (e.g., between biotin-avidin/streptavidin interaction, or through magnetic field), or covalent coupling. Certain reversible coupling can allow the captured cells to be eluded from the affinity support. For instance, if the complex is biotinylated with Biotin HPDP, the biotin moiety can be cleaved from the reacted sulfhydryl with a reducing reagent (e.g., DDT, or β-mercaptoethanol).

The new class I multimers can also be used to characterize T cells that recognize non-classical class I proteins. This is because the new β2-M can assemble with a wide variety of class I heavy chains, and thus a wide variety of class I multimer probes can be generated using the new β2-M.

The HLA class I gene family (see, e.g., "Phylogeny of the Major Histocompatibility Complex," in *Immunological Reviews*, 113:1–241, 1990) includes the highly polymorphic class I genes HLA-A, HLA-B and HLA-C, all of which show widespread tissue expression. At least three additional class I genes HLA-E, HLA-F and HLA-G (known as non-classical class I b genes) have been identified; these genes are highly homologous to the classical HLA class I genes, and their polypeptide products are all associated with β2-M. The family of non-classical class I genes also includes members that do not reside in the MHC genomic complex, such as the subfamily of CD1 genes in both mouse and human, and the mouse thymus leukemia (TL) antigen. Both the TL antigen and CD1 proteins have the typical structure of an antigen-presenting class I molecule. They form heterodimers at the cell surface in which α heavy chain of approximately 38–50 kDa interacts with β2-M. Another notable non-classical class I gene in mice is the Qa-2 gene. The Qa-2 products, like other class I heavy chains, are associated with β2-M. The function of these non-classical molecules and the responding T cells are largely unknown.

The ability of β2-M to associate with diverse heavy chains, and the use of these complexes as signal (e.g., fluorescence)-producing probes, can facilitate the characterization of the T cells that react with these class I molecules. Information about the corresponding T cells may provide important clues about their specialized function in the immune system.

Monomeric class I complexes conjugated to a solid support are in effect multimerized due to their physical proximity. Thus, the new, monomeric class I complexes conjugated to a solid surface via their free —SH groups can also be used for the same purposes as those described above for multimeric class I complexes.

The following examples describe the generation and some uses of several new class I MHC-peptide tetramers. The examples serve to illustrate, but not limit, the new methods and reagents.

In these examples, CTL clones from asymptomatic HIV-1 seropositive patients were established and maintained as described (Johnson et al., *J. Immunol*, 147:1512–1521, 1991). HLA-typing was performed by the Massachusetts General Hospital Tissue Typing Laboratory using standard serological techniques. H-2K$^b$-SV9 specific CTL clones (syngeneic reactive) were generated in H-2$^b$ mice (K$^b$D$^b$) as described (Zhou et al., *J. Immunol Methods*, 153:193–200, 1992). The alloreactive CTL were derived from H-2$^{dm2}$ mice (K$^d$D$^d$). All CTLs were maintained in culture by periodic stimulation with RMA-S cells (H-2$^b$; see, e.g., Townsend et al., *Cold Spring Harb. Symp. Quant. Biol.*, 54 Pt 1:299–308, 1989) loaded with SV9 peptide. CTL clone 4G3, which arose in an H-2K$^b$ mouse, reacts specifically with the ovalbumin octapeptide pOVA (SIINFEKL; SEQ ID NO: 12) in association with H-2K$^b$ (Walden et al., *Proc. Natl. Acad. Sci. USA*, 87:9015–9019, 1990). Cell surface MHC class I molecules on RMA-S cells are largely devoid of peptide unless loaded with peptides from the external medium (Heemels et al., *Ann. Rev. Biochem.*, 64:463–491 1995).

EXAMPLE 1
Production of a Mutant β2-M

The ribosome-binding site and coding region from a β2-M expression plasmid (Garboczi et al., *Proc. Natl. Acad. Sci. USA*, 89:3429–2433, 1992) was cloned into the *E. coli* expression vector pLM1 (Garboczi et al., *J. Immunol.*, 157:5403–5410, 1996) to achieve a higher protein yield. The β2-M polypeptide is of human origin and has 99 amino acid residues (SEQ ID No: 1) plus one additional methionine residue at the N-terminus that results from the expression in *E. coli*.

A cysteine residue was substituted for the tyrosine 67 residue in the polypeptide by using overlap extension PCRs (i.e., polymerase chain reactions). Four PCR primers were used. The first two were used at the 5' and 3' ends of the β2-M coding region in the pHN1 plasmid (Garboczi et al., *Proc. Natl. Acad. Sci. USA*, 89:3429–3433, 1992). These two primers were the 5' primer CTAGAGGATCCTCACA-CAGGAAACAGAATTTCGAG (SEQ ID NO: 4) and the 3' primer CCACCGCGCTACTGCCGCCAGGC (SEQ ID NO: 5). The 5' primer introduced a new BamHI site at the 5' end of the β2-M coding region. The other two primers were used for mutagenesis. They were the top strand primer CTC TTG TAC <u>TGC</u> ACT GAA TTC ACC CCC (SEQ ID NO: 6), and the bottom strand primer GAA TTC AGT <u>GCA</u> GTA CAA GAG ATA GAA (SEQ ID NO: 7). The new cysteine codon and its complement are underlined.

To generate the cysteine mutation, the following two pairs of primers were first used on the pHN1 template to yield two PCR products: (i) the 5' primer and the bottom strand primer, and (ii) the 3' primer and the top strand primer. The two PCR products were electrophoresed and purified from agarose gel. They were then subjected together to a PCR reaction using the 5' and 3' primers. The final PCR product, which contains the β2-M coding region with the cysteine mutation, was digested with BamHI and HindIII and cloned into the same sites in pLM1. The mutated β2-M (i.e., "β2-M(Cys67)") sequence was confirmed by DNA sequencing. Plasmid pLM1 bearing the β2-M(Cys67)-coding sequence was transformed into *E. coli* host BL21(DE3)plysS (Studier et al., *Methods Enzymol.*, 185:60–89,1990), and a large amount of β2-M(Cys67) was obtained in the form of inclusion body protein.

EXAMPLE 2
Generation of Peptide-MHC Tetramer

To generate a class I MHC-peptide tetramer, the tyrosine residue at position 67 (SEQ ID NO: 1) of human β2-M was first replaced with a cysteine residue, using standard mutagenesis techniques (see above). There are two naturally occurring cysteine residues in β2-M, which maintain the immunoglobulin structure of β2-M by forming a di-sulfide bond. The new cysteine residue did not bond with any one of the natural cysteine residues, allowing the proper folding of the mutant β2-M ("β2-M(Cys67)"). The free sulfhydryl group in the new cysteine residue was to be used for subsequent chemical modifications of the β2-M subunit.

A monomeric mutant HLA-A2 containing β2-M(Cys67) was then generated. The HLA-A2 heavy chain and the mutant β2-M subunit was obtained in large amounts from *E. coli* host cells transformed with the respective expression vectors. The formation of HLA-A2 (subtype A0201) was initiated in a dilute solution containing a denatured HLA-A2 heavy chain (1 μM), the denatured β$_2$-M(Cys67) polypeptide (2 μM), and a synthetic peptide (10 μM) (see, e.g., Garboczi et al., *Proc. Natl. Acad. Sci. USA*, 89:3429–3433, 1992). The folded MHC-peptide complexes were purified by HPLC (i.e., high performance liquid chromatography) gel filtration. The protein concentration of the purified complex was determined by measuring its optical density. For HLA-A2, 1 A$_{280}$ unit represents 0.67 mg ml$^{-1}$ of the protein. The solvent-accessible cysteine 67 in the mutant β2-M subunit was maintained in a reduced state by 0.1 mM DDT.

The monomeric mutant HLA-A2 was then biotinylated with iodoacetyl-LC-biotin ("ILB"; Pierce), a sulfhydryl-reactive reagent, at the cysteine 67 residue of β2-M(Cys67). ILB, which was dissolved in N,N-dimethyl-formamide, was applied at a 5-fold molar excess over the total amount of cysteine in solution. The biotinylation reaction was carried out in Tris-HCl (pH 8.0) and 0.1 mM DDT, and the reaction lasted for 1 hour in the dark at room temperature. Subsequent to the reaction, the volume of the reaction mix was reduced with CENTRICON 30 from 0.5–1 ml to 50 μl, diluted again in 1 ml Tris-HCl (pH 8.0), concentrated to about 100 μl, and purified by HPLC gel filtration. In the biotinylated β2-M(Cys67), the biotin moiety of ILB was separated from the sulfhydryl group of the cysteine 67 residue by the long iodoacetyl-LC arm.

The biotinylated MHC-peptide complexes were purified by HPLC gel filtration. The purified complexes were then multimerized in the presence of deglycosylated avidin-phycoerythrin ("avidin-PE"; Molecular Probes). Deglycosylated avidin-PE binds more than 12 μg of biotin per mg protein. The resulting tetrameric MHC-peptide complexes were subjected to HPLC gel filtration (TSK G 3000SW, TOSO HAAS, Gel Filtration Standard/BIO-RAD) and then concentrated (CENTRICON 100, Amicon).

EXAMPLE 3
Labeling of T cells with a Peptide-Class I Tetramer

A peptide-MHC class I tetramer was prepared with a HIV-1 gag peptide (i.e., SL9, whose sequence is SLYNT-VATL (SEQ ID NO: 8)) (Johnson et al., *J. Immunol*, 147:1512–1521, 1991), and a control peptide from HIV reverse transcriptase (i.e., IV9, whose sequence is ILKEPVHGV (SEQ ID NO: 9)) (Tsomides et al., *Proc. Natl. Acad. Sci. USA*, 88:11276–11280 1991). The tetramer was formed by use of avidin-PE, as described in the preceding Example. The binding of the tetramer to cytotoxic T lymphocyte ("CTL") clones with known antigen-binding specificity was monitored by flow cytometry.

Specifically, 5×10$^5$ cells from each of three human CTL clones specific for HIV-1 derived peptides were prestained with an anti-CD8 monoclonal antibody ("mAb") Cy-Chrome (Pharmingen). These three clones, i.e., 68A62 (Tsomides et al., *Proc. Natl. Acad. Sci. USA,* 88:11276–11280, 1991), 18030 (Johnson et al., J. Immunol., 147:1512–1521, 1991), 63D35 are specific for HLA-A2-IV9 (i.e., IV9 presented by HLA-A2), HLA-A2-SL9, and HLA-B11-AK9 (AK9: a HIV-1 reverse transcriptase peptide with the sequence of AIFQSSMTK (SEQ ID NO: 10)), respectively.

The pre-stained cells were then incubated with the soluble, PE-labeled tetrameric HLA-A2-SL9 complex at a concentration of 50 µg/100 µl RPMI at 4° C. for an hour. The cells were washed and subjected to FACS (i.e., fluorescence-activating cell sorting) analysis using a FACSCAN flow cytometer (Becton Dickinson).

In the FACS analysis, contour plots were based on 10,000 events gated on forward- versus side-scatter. An arbitrarily set boundary on the PE-fluorescence intensity of a negative control was the position of the X-axis quadrant marker, implying that about 80% of the cells can be considered as positive for PE-fluorescence.

Figure 1B:
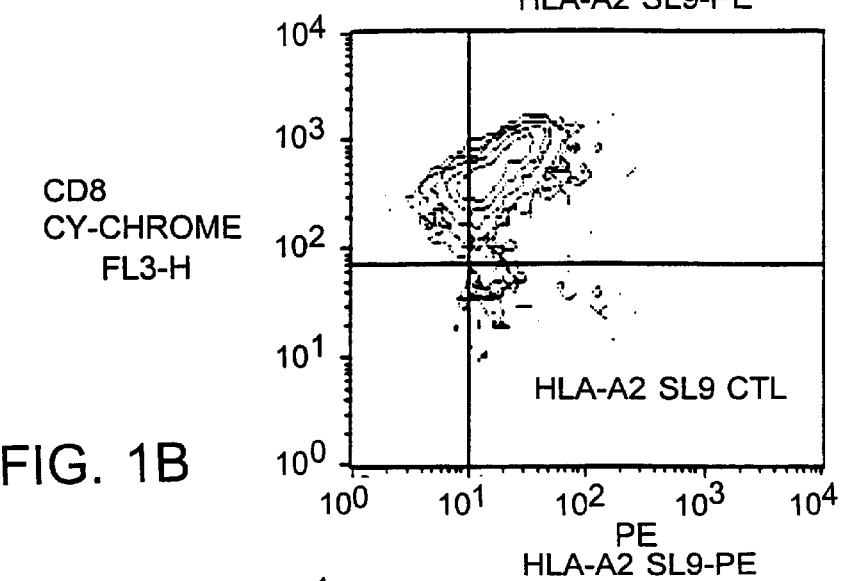
Figure 1C:
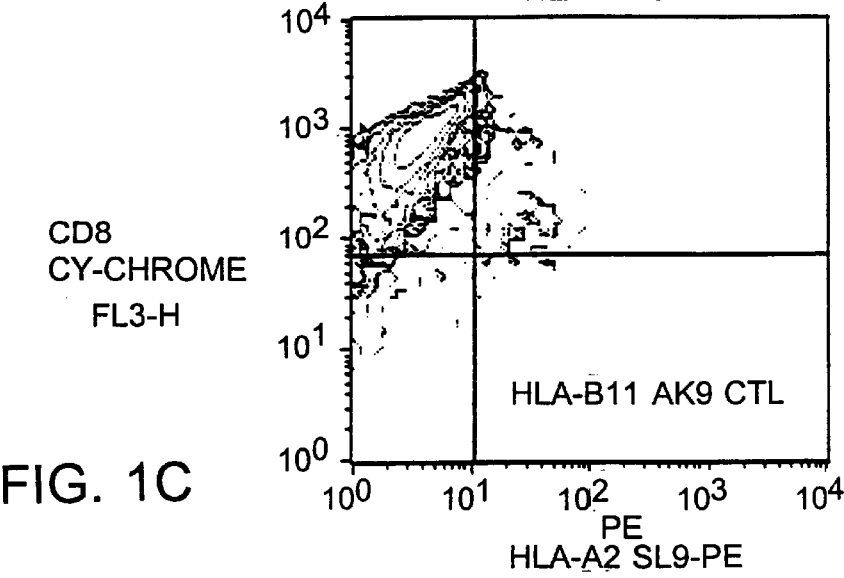

The data showed that there was a 10-fold increase in the PE fluorescence intensity when the PE-labeled tetramer stained CTLs of clone 18030 (FIG. 1B), as compared to CTLs of clones 68A82 and 63D35 (FIGS. 1A and 1C). Thus, the staining of CTLs by the HLA-A2-SL9 tetramer was specific.

A similar shift of PE fluorescence intensity was observed with CTLs of clone 68A62 when those CTLs were stained with a HLA-A2-IV9 tetramer.

Based on quadrant markers, about 80% of the CTLs specific for HLA-A2-SL9 were stained positively with the phycoerythrin-labeled tetramer.

EXAMPLE 4

Labeling of T Cells with a Hybrid Peptide-Class I Complex

The mutant human β2-M in which Tyr 67 has been replaced with a cysteine residue was also shown to bind stably to the heavy chains of the mouse MHC class I molecule $K^b$.

Tetrameric MHC class I molecules were generated with use of a purified murine H-2$K^b$ ("$K^b$") heavy chain (Zhang et al., *Proc. Natl. Acad. Sci. USA,* 89:8403–8407, 1992), the mutant human β2-M, and SV9, a Sendai virus nucleoprotein-derived peptide (FAPGNYPAL, SEQ ID NO: 11) (Kast et al., *Proc. Natl. Acad. Sci. USA,* 88:2283–2287, 1991; and Schumacher et al., *Nature,* 350:703–706, 1991). SV9 promoted folding of the hybrid $K^b$ molecule with an efficiency similar to that of SL9 for promoting folding of HLA-A2. The purified $K^b$ tetramer migrated as a single peak on gel filtration HPLC. The presence of the heavy chain and the β2-M subunit in the peak fractions was confirmed by SDS polyacrylamide gel electrophoresis. 5×10⁵ murine CTLs of three different clones were pre-stained with anti-CD8 TRI-COLOR (CALTAG), and then incubated with 50 µg/100 µl RPMI PE-labeled chimeric H-2$K^b$-SV9 tetramer for an hour at 4° C. The three CTL clones 2F3, 3C2, and 4G3 (Walden et al., *Proc. Natl. Acad. Sci. USA,* 87:9015–9019, 1990) are specific for SV9 bound to H-2$K^b$, SV9 bound to H-2Db, and OVA (SIINFEKL, SEQ ID NO: 12); derived from ovalbumin; Walden et al., Proc. Natl. Acad. Sci. USA, 87:9015–9019) bound to H-2$K^b$, respectively. (The specificity of the clones is determined on the basis of their lysis of target cells loaded with the corresponding peptide.) After the incubation, the cells were washed and subjected to FACS analysis.

Figure 2A:
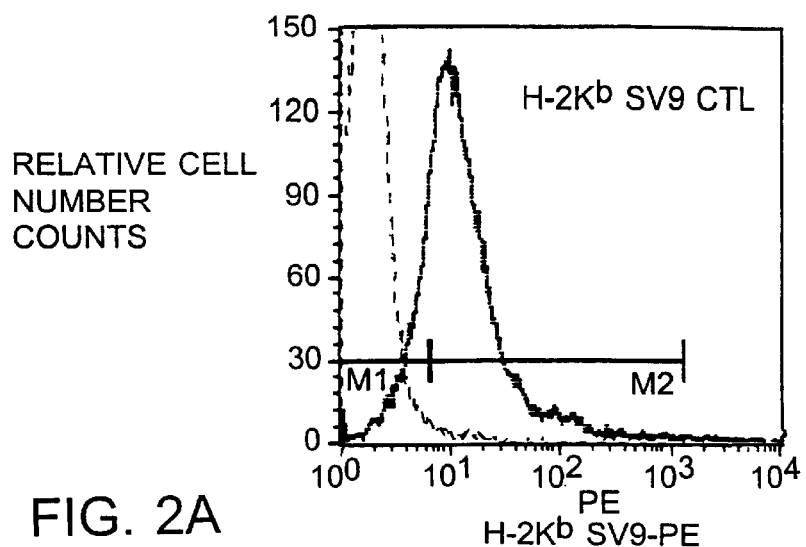
FIGS. 2A–2C are a set of graphs showing the results of flow cytometry analysis of the binding of the phycoerythrin-labeled chimeric H-2K$^b$-SV$^9$ tetramer to mouse cytotoxic T lymphocytes of clones 2F3 (specific for the SV9 peptide bound to H-2K$^b$), 3C2 (specific for the SV9 peptide bound to H-2D$^b$), and 4G3 (specific for the OVA peptide bound to H-2K$^b$), respectively. The staining intensity of the H-2K$^b$-SV9 tetramer is shown in solid line, and the intensity of background fluorescence (i.e., staining with avidin-PE only) is shown in dashed line.

Histogram plots (FIGS. 2A–2C) for the FACS analysis were based on 10,000 events gated on CD8 fluorescence. As shown in the plots, the $K^b$-SV9 tetramer stained only 2F3 CTLs (FIG. 2A), but not 3C2 (FIG. 2B) or 4G3 (FIG. 2C) CTLs.

Figure 2B:
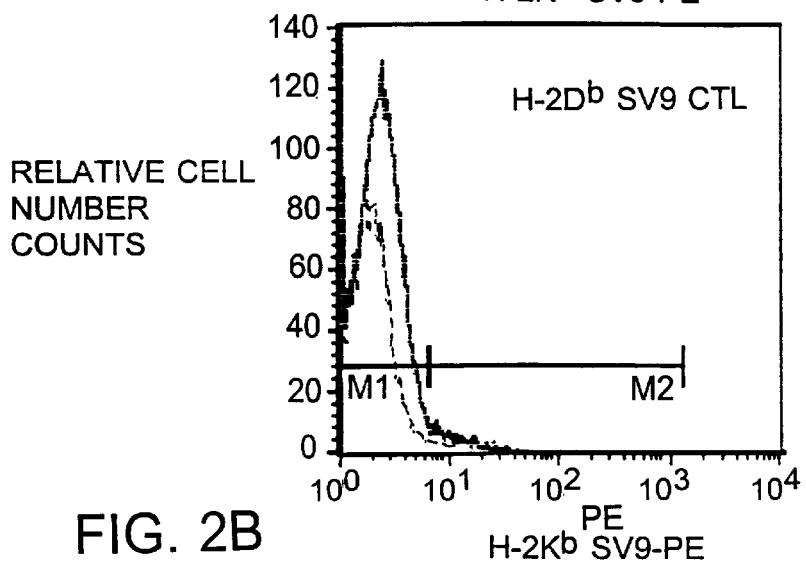
Figure 2C:
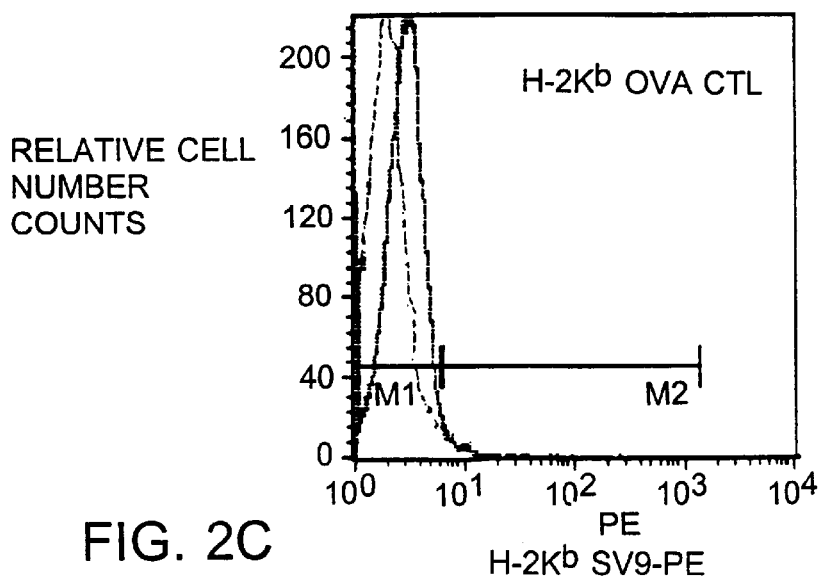

In the FACS analysis, markers (M1, M2) were placed to delineate a region of positive intensity relative to a control (FIGS. 2B and 2C). Based on these markers, 78% of 2F3 CTLs (FIG. 2A) were found to stain positive with the $K^b$-SV9 tetramer.

EXAMPLE 5

Binding of T Cells by Allogeneic Peptide-Class I Complexes

Allograft rejection is probably the most powerful T cell reaction known. During such a rejection, an individual's T cells respond strongly to target cells (e.g., a skin graft from a genetically disparate individual of the same species) that bear allogeneic MHC molecules. It has been suggested that the affinities of T cell receptors for MHC-peptide complexes be higher when the MHC component is allogeneic (i.e., non-self) than syngeneic (i.e., self) Sykulev et al., *Proc. Natl. Acad. Sci. USA,* 91:11487–11491, 1994 and Eisen et al., Advances in Protein Chemistry, 49:1–56, 1996).

FIGS. 3A–3D compare the reactivity of the $K^b$-SV9 tetramer with murine CD8⁺ CTLs from two different mouse lines. Briefly, 5×10⁵ syngeneic MHC- and allogeneic MHC-CTLs were stained with anti-CD8 TRI-COLOR and anti-H-2$K^b$-FITC mAbs (CALTAG), washed and FACS analysed. The CTLs were then incubated with the H-2$K^b$ SV9 tetramer-PE reagent (50 µg/100 µl RPMI, 4° C., 1 h), washed, and again subjected to FACS analysis. All three fluorochromes were excited with an argon laser in a single laser instrument (total of 10,000 events collected).

Figure 3A:
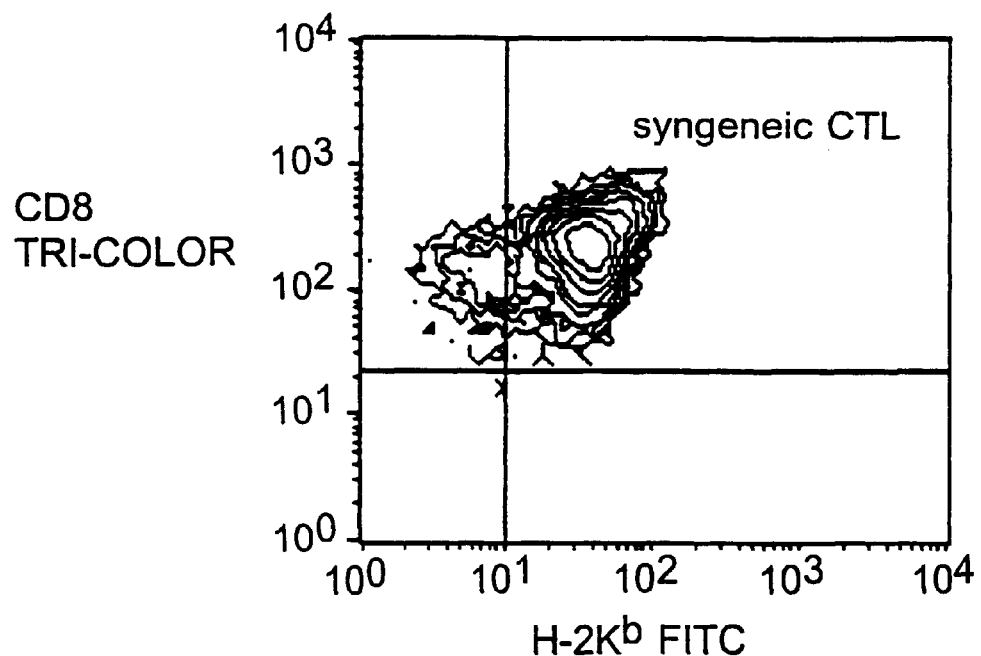
FIGS. 3A and 3B are a set of graphs showing the binding of a tetrameric MHC-peptide complex (H-2K$^b$ complexed with SV9) to CTLs where K$^b$ is syngeneic (FIG. 3A) or allogeneic (FIG. 3B). Dual parameter contour plots in FIGS. 3A and 3C illustrate the phenotype (anti-CD8 versus anti-H-2K$^b$) of CTLs (double positive) generated in H-2$^b$ mice and CTLs (single positive) generated in H-2$^d$ mice, respectively. The staining intensities with the H-2K$^b$ SV9 reagent (bold line) in FIGS. 3A and 3C are shown in FIGS. 3B and 3D, respectively, in comparison with background intensity (avidin-PE only, dashed line). Note the comparable shift of fluorescence intensity for syngeneic (FIG. 3B) and the majority of the allogeneic CTL (FIG. 3D).
Figure 3B:
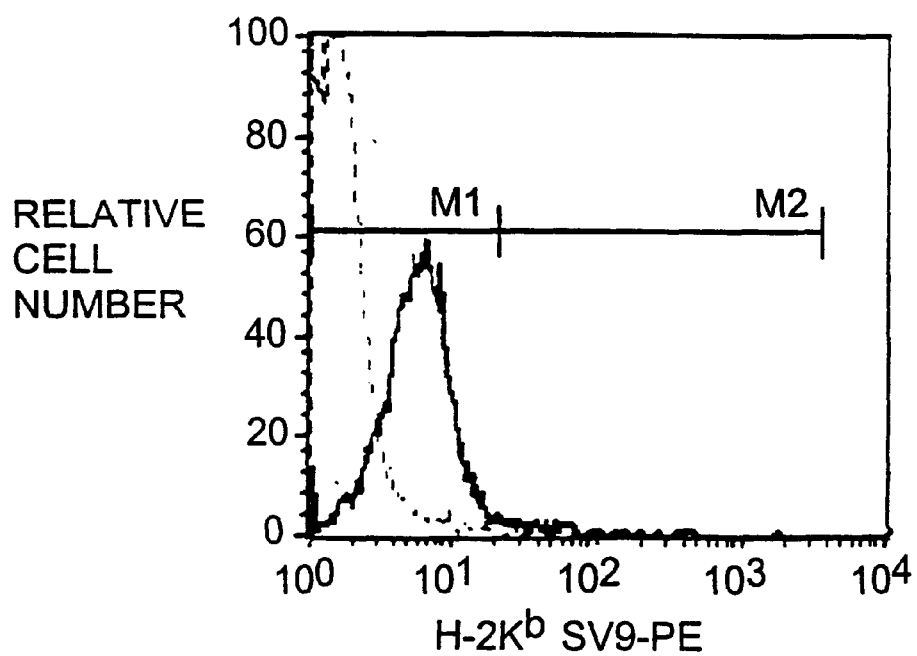
Figure 3C:
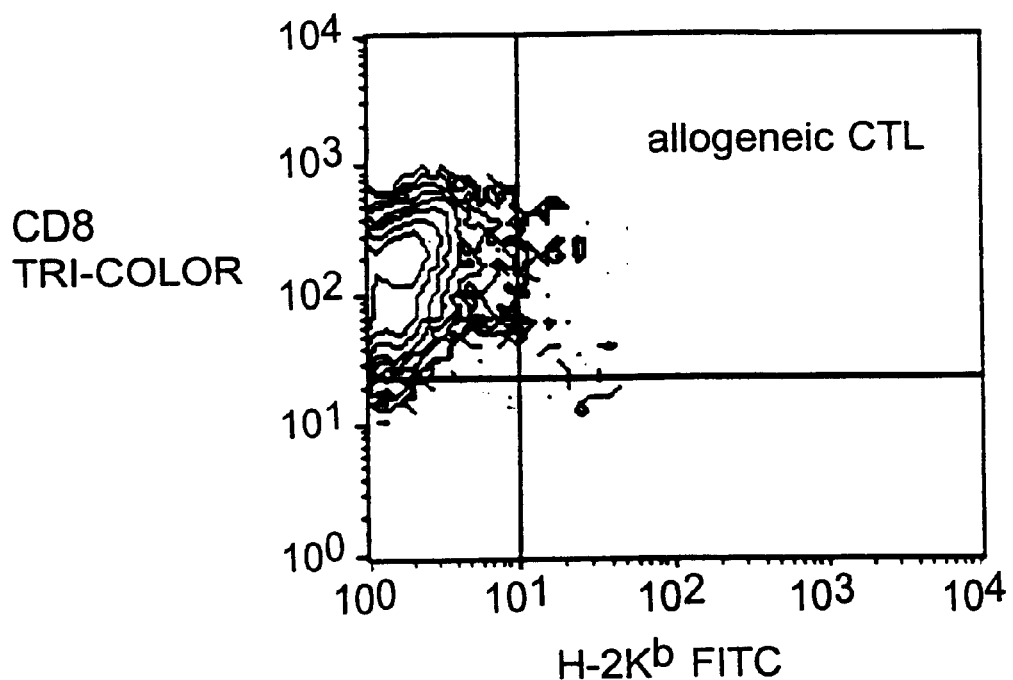
Figure 3D:
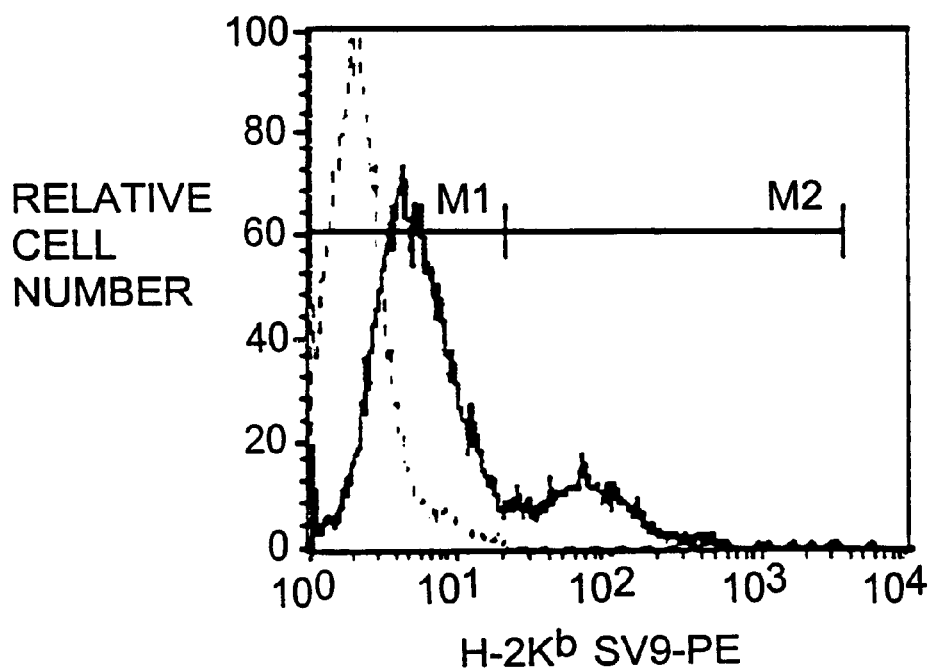

The CTLs in FIG. 3A were derived from a $K^b$-positive mouse and the reaction shown is syngeneic; whereas in FIG. 3C, the CTLs were derived from a $K^b$-negative mouse and the reaction shown is allogeneic. The tetramer bound specifically to CTLs from both mouse lines (FIGS. 3B and 3D), but it distinguished between two subsets in the alloreactive CTLs (FIG. 3D), the better binding subset amounting to about 12–15% of the total CTL population. The observed difference in staining intensities of CTLs (FIG. 3D) might be influenced by differences in cell surface density of TCR and perhaps CD8 molecules. Assuming a 1:1 ratio of the TCR heterodimer with the CD3 complex, CD3 and CD8 expression levels were analyzed. The analysis showed that the cellular subsets of the allogeneic CTL line that stained with multimeric $K^b$-SV9 of different intensities had the same amount of CD8 and CD3 per cell.

OTHER EMBODIMENTS

It is to be understood that while the invention has been described in conjunction with the detailed description thereof, the foregoing description is intended to illustrate and not limit the scope of the invention, which is defined by the scope of the appended claims. For example, to attach a foreign class I molecule (e.g., one with an allogeneic or even xenogeneic heavy chain) to a tumor cell, a ligand for a receptor specifically expressed on the tumor cell, instead of a tumor-specific antibody, is conjugated to the foreign MHC class I molecule to direct an alloresponse to the tumor tissue.

Other aspects, advantages, and modifications are within the scope of the following claims.

What is claimed is:

1. A method of preparing a conjugate of a MHC class I molecule and a compound, the method comprising:

providing a MHC class I molecule, wherein, in the β2-microglobulin subunit of the MHC class I molecule, a residue corresponding to position 91 or 52 of SEQ ID NO: 1 has been substituted with a cysteine residue; and conjugating the MHC class I molecule and the compound specifically via a linkage formed between the sulfhydryl group of the cysteine reside in the β2-microglobulin subunit and a functional group of the compound.

2. The method of claim 1, wherein the compound is a ligand for a multivalent binding molecule.

3. The method of claim 1, wherein the compound is an antibody.

4. The method of claim 3, wherein the antibody is specific for a tumor antigen.

5. The method of claim 1, wherein the compound is on the surface of a cell.

6. The method of claim 5, wherein the compound is a protein.

7. The method of claim 5, wherein the cell is an antigen-presenting cell.

8. The method of claim 1, wherein the compound is a ligand for a surface receptor of a cell.

9. The method of claim 8, wherein the cell is an antigen-presenting cell.

10. The method of claim 1, wherein a residue corresponding to position 91 of SEQ ID NO: 1 has been substituted with a cysteine residue.

11. The method of claim 1, wherein a residue corresponding to position 52 of SEQ ID NO: 1 has been substituted with a cysteine residue.

12. A method of making a multimeric MHC class I molecule, the method comprising:

providing a conjugate of a monomeric MHC class I molecule and a ligand for a multivalent binding molecule, wherein, in the β2-microglobulin subunit of the MHC class I molecule, a residue corresponding to position 91 or 52 of SEQ ID NO: 1 has been substituted with a cysteine residue and the conjugate is formed specifically via a linkage between the sulfhydryl group of the cysteine residue in the β2-microglobulin subunit and a functional group of the ligand; and attaching a plurality of the conjugates, via the ligand, to the multivalent binding molecule to form a multimeric MHC class I molecule.

13. The method of claim 12, wherein the ligand is biotin, and the multivalent binding molecule is streptavidin or avidin.

14. The method of claim 12, wherein a residue corresponding to position 91 of SEQ ID NO: 1 has been substituted with a cysteine residue.

15. The method of claim 12, wherein a residue corresponding to position 52 of SEQ ID NO: 1 has been substituted with a cysteine residue.

16. A method of making a multimeric MHC class I molecule, the method comprising:

providing a β2-microglobulin into which a cysteine residue is substituted for a residue corresponding to position 91 or 52 of SEQ ID NO: 1;

conjugating the β2-microglobulin and a ligand for a multivalent binding molecule, specifically via a linkage formed between the sulfhydryl group of the cysteine residue in the β2-microglobulin and a functional group of the ligand;

mixing the conjugate so obtained with an α chain of an MHC class I molecule to form a monomeric MHC class I molecule; and attaching a plurality of the monomeric MHC class I molecules so obtained to the multivalent binding molecule, via the ligand, to form a multimeric MHC class I molecule.

17. The method of claim 16, wherein the ligand is biotin, and the multivalent binding molecule is streptavidin or avidin.

18. The method of claim 16, wherein a cysteine residue is substituted for a residue corresponding to position 91 of SEQ ID NO: 1.

19. The method of claim 16, wherein a cysteine residue is substituted for a residue corresponding to position 52 of SEQ ID NO: 1.

20. A MHC class I conjugate comprising a MHC class I molecule, wherein, in the β2-microglobulin subunit of the MHC class I molecule, a residue corresponding to position 91 or 52 of SEQ ID NO: 1 has been substituted with a cysteine residue; and a compound conjugated to the MHC class I molecule specifically via a linkage formed between the sulfhydryl group of the cysteine reside in the β2-microglobulin subunit and a functional group of the compound.

21. The conjugate of claim 20, wherein the compound is a ligand for a multivalent binding molecule.

22. The conjugate of claim 21, further comprising the multivalent binding molecule and at least one other MHC class I molecule attached to the multivalent binding molecule.

23. The conjugate of claim 20, wherein the compound is an antibody.

24. The conjugate of claim 23, wherein the antibody is specific for a tumor antigen.

25. The conjugate of claim 20, wherein the compound is on the surface of a cell.

26. The conjugate of claim 25, wherein the compound is a protein.

27. The conjugate of claim 25, wherein the cell is an antigen-presenting cell.

28. The conjugate of claim 20, wherein the compound is a ligand for a surface receptor of a cell.

29. The conjugate of claim 28, wherein the cell is an antigen-presenting cell.

30. The conjugate of claim 20, wherein a residue corresponding to position 91 of SEQ ID NO: 1 has been substituted with a cysteine residue.

31. The conjugate of claim 20, wherein a residue corresponding to position 52 of SEQ ID NO: 1 has been substituted with a cysteine residue.

* * * * *

SEQUENCE LISTING

<160> NUMBER OF SEQ ID NOS: 12

<210> SEQ ID NO: 1
<211> LENGTH: 100
<212> TYPE: PRT
<213> ORGANISM: Homo sapiens

<400> SEQUENCE: 1

Met Ile Gln Arg Thr Pro Lys Ile Gln Val Tyr Ser Arg His Pro Ala
 1               5                  10                  15

Glu Asn Gly Lys Ser Asn Phe Leu Asn Cys Tyr Val Ser Gly Phe His
                20                  25                  30

Pro Ser Asp Ile Glu Val Asp Leu Leu Lys Asn Gly Glu Arg Ile Glu
            35                  40                  45

Lys Val Glu His Ser Asp Leu Ser Phe Ser Lys Asp Trp Ser Phe Tyr
        50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met
            100

<210> SEQ ID NO: 2
<211> LENGTH: 10
<212> TYPE: PRT
<213> ORGANISM: Influenza virus

<400> SEQUENCE: 2

Ile Leu Gly Phe Val Phe Thr Leu Thr Val
 1               5                  10

<210> SEQ ID NO: 3
<211> LENGTH: 10
<212> TYPE: PRT
<213> ORGANISM: Influenza virus

<400> SEQUENCE: 3

Lys Leu Gly Glu Phe Tyr Asn Gln Met Met
 1               5                  10

<210> SEQ ID NO: 4
<211> LENGTH: 35
<212> TYPE: DNA
<213> ORGANISM: Homo sapiens

<400> SEQUENCE: 4
ctagaggatc ctcacacagg aaacagaatt tcgag                                35

<210> SEQ ID NO: 5
<211> LENGTH: 23
<212> TYPE: DNA
<213> ORGANISM: Homo sapiens

<400> SEQUENCE: 5
ccaccgcgct actgccgcca ggc                                             23

<210> SEQ ID NO: 6
<211> LENGTH: 27
<212> TYPE: DNA

```
<213> ORGANISM: Homo sapiens

<400> SEQUENCE: 6
ctcttgtact gcactgaatt caccccc                                27

<210> SEQ ID NO: 7
<211> LENGTH: 27
<212> TYPE: DNA
<213> ORGANISM: Homo sapiens

<400> SEQUENCE: 7
gaattcagtg cagtacaaga gatagaa                                27

<210> SEQ ID NO: 8
<211> LENGTH: 9
<212> TYPE: PRT
<213> ORGANISM: Human immunodeficiency virus type 1

<400> SEQUENCE: 8

Ser Leu Tyr Asn Thr Val Ala Thr Leu
  1               5

<210> SEQ ID NO: 9
<211> LENGTH: 9
<212> TYPE: PRT
<213> ORGANISM: Human immunodeficiency virus type 1

<400> SEQUENCE: 9

Ile Leu Lys Glu Pro Val His Gly Val
  1               5

<210> SEQ ID NO: 10
<211> LENGTH: 9
<212> TYPE: PRT
<213> ORGANISM: Human immunodeficiency virus type 1

<400> SEQUENCE: 10

Ala Ile Phe Gln Ser Ser Met Thr Lys
  1               5

<210> SEQ ID NO: 11
<211> LENGTH: 9
<212> TYPE: PRT
<213> ORGANISM: Sendai virus

<400> SEQUENCE: 11

Phe Ala Pro Gly Asn Tyr Pro Ala Leu
  1               5

<210> SEQ ID NO: 12
<211> LENGTH: 8
<212> TYPE: PRT
<213> ORGANISM: Mus musculus

<400> SEQUENCE: 12

Ser Ile Ile Asn Phe Glu Lys Leu
  1               5
```